(12) United States Patent
Zhang et al.

(10) Patent No.: US 11,913,930 B2
(45) Date of Patent: Feb. 27, 2024

(54) BISMUTH OXIDE BASED AMMONIA SENSOR

(71) Applicant: Qingdao University, China, Qingdao (CN)

(72) Inventors: Kewei Zhang, Qingdao (CN); Mingxin Zhang, Qingdao (CN); Yanzhi Xia, Qingdao (CN); Bin Hui, Qingdao (CN); Anqin Zhou, Qingdao (CN)

(73) Assignee: QINGDAO UNIVERSITY, CHINA, Shandong (CN)

( * ) Notice: Subject to any disclaimer, the term of this patent is extended or adjusted under 35 U.S.C. 154(b) by 132 days.

(21) Appl. No.: 17/716,519

(22) Filed: Apr. 8, 2022

(65) Prior Publication Data

US 2022/0326205 A1    Oct. 13, 2022

(30) Foreign Application Priority Data

Apr. 8, 2021 (CN) .......................... 202110387103.8
Nov. 17, 2021 (GB) ...................................... 2116586

(51) Int. Cl.
*G01N 33/00* (2006.01)
*G01N 33/497* (2006.01)
*G01N 33/50* (2006.01)

(52) U.S. Cl.
CPC ....... *G01N 33/0054* (2013.01); *G01N 33/497* (2013.01); *G01N 33/50* (2013.01)

(58) Field of Classification Search
CPC ............. G01N 33/497; G01N 33/0054; G01N 33/4972; G01N 2021/1704;
(Continued)

(56) References Cited

U.S. PATENT DOCUMENTS

| 2004/0118703 | A1* | 6/2004 | Wang | ................. G01N 33/0054 |
| | | | | 204/426 |
| 2004/0234962 | A1* | 11/2004 | Alarcon | ................. G01N 33/68 |
| | | | | 435/6.11 |

(Continued)

FOREIGN PATENT DOCUMENTS

| CN | 102995336 A | * | 3/2013 |
| CN | 105463672 A | * | 4/2016 |

(Continued)

OTHER PUBLICATIONS

M. Janarthanan et al., "The properties of bioactive substances obtained from seaweeds and their applications", Journal of Industrial Textiles, vol. 48, No. 1, Feb. 9, 2017. (Year: 2017).*

(Continued)

*Primary Examiner* — David A. Rogers
(74) *Attorney, Agent, or Firm* — MUNCY, GEISSLER, OLDS & LOWE, PC

(57) ABSTRACT

A bismuth oxide material with a hierarchical structure in gas detection used for detecting the content of low-concentration ammonia in an environment. The bismuth oxide material with the hierarchical structure integrally presents a microsphere shape. The diameter of the microsphere is 1-3 μm. The bismuth oxide material is formed by self-assembling lamellar structure units with the thickness of 10-80 nm. The bismuth oxide material is made into a gas sensor with high sensitivity and selectivity to ammonia gas at room temperature, which is suitable for detecting trace harmful gas in the environment. The gas sensor made of bismuth oxide does not need to be heated when in use, so that the heating step of the conventional gas sensor is omitted, and the gas sensor can be directly placed in a normal-temperature environment for operation. The method is simple, easy to operate, high in efficiency and wide in application prospect.

13 Claims, 11 Drawing Sheets

(58) Field of Classification Search
CPC ....... G01N 2033/4977; G01N 33/0027; G01N 33/98; G01N 2021/7759
See application file for complete search history.

(56) References Cited

U.S. PATENT DOCUMENTS

| | | | | |
|---|---|---|---|---|
| 2005/0014290 | A1* | 1/2005 | Hsieh | G01N 33/66 436/518 |
| 2009/0301878 | A1* | 12/2009 | Wang | G01N 33/0054 204/429 |
| 2022/0061823 | A1* | 3/2022 | Berger | G01N 33/497 |

FOREIGN PATENT DOCUMENTS

| | | | | | |
|---|---|---|---|---|---|
| CN | 106814111 | A | * | 6/2017 | |
| CN | 105420920 | B | * | 8/2018 | ............... D01D 5/06 |
| CN | 109875795 | A | * | 6/2019 | |
| CN | 111346255 | A | * | 6/2020 | ....... A61F 13/00029 |
| CN | 211658503 | U | * | 10/2020 | |
| JP | 5083898 | B2 | * | 11/2012 | ......... G01N 27/4075 |
| JP | 2015197387 | A | * | 11/2015 | |
| JP | 2020520781 | A | * | 7/2020 | |
| WO | WO-2007089328 | A2 | * | 8/2007 | .............. A61B 5/082 |

OTHER PUBLICATIONS

S. Rajaboopathi et al., "Evaluation of UPF and antibacterial activity of cotton fabric coated with colloidal seaweed extract functionalized silver nanoparticles", Journal of Photochemistry & Photobiology, B: Biology, Apr. 18, 2018. (Year: 2018).*

Mingxin Zhang et al., "Porous Oxide-Functionalized Seaweed Fabric as a Flexible Breath Sensor for Noninvasive Nephropathy Diagnosis", ACS Sensors, No. 7, Aug. 19, 2022. (Year: 2022).*

Zhe Xing et al., "Recent Advances in Wearable Sensors for the Monitoring of Sweat: A Comprehensive Tendency Summary", Chemosensors, Aug. 23, 2023. (Year: 2023).*

Li, et al., "Flexible Room-Temperature NH3 Sensor for Ultrasensitive, Selective, and Humidity-Independent Gas Detection", 2018, pp. 27858-27867, ACS Appl. Mater. Interfaces.

Davies et al., "Quantitative analysis of ammonia on the breath of patients in end-stage renal failure", Aug. 1997, pp. 223-228, vol. 52, Kidney Int.

Srivastava, "Highly sensitive NH3 sensor using Pt catalyzed silica coating over WO3 thick films", Jan. 2008, pp. 46-52, Sensors and Actuators, B 2008, 133.

Xiong, "Ultra-sensitive NH3 sensor based on flower-shaped SnS2 nanostructures with sub-ppm detection ability", 2018, pp. 159-167, Journal of Hazardous Materials, 341.

Gao, et al., "NH3 Sensor Based on 2D Wormlike Polypyrrole/Graphene Heterostructures for a Self-Powered Integrated System", 2020, pp. 38674-38681, ACS Appl. Material and Interfaces, 12.

Liu, et al., "Controllable synthesis of a-Bi2O3 and g-Bi2O3 with high photocatalytic activity by a-Bi2O3/g-Bi2O3/a-Bi2O3 transformation in a facile precipitation method", 2016, pp. 787-799, Journal of Alloys and Compounds, 689.

Lu, et al., "A high-performance Bi2O3/Bi2SiO5 p-n heterojunction photocatalyst induced by phase transition of Bi2O3", 2018, pp. 59-67, Applied Catalysis B: Environmental, 237.

Kim, et al., "Selective NO2 sensor based on Bi2O3 branched SnO2 nanowires", 2018, pp. 356-369, Sensors and Actuators, B: Chemical, 274.

* cited by examiner

BISMUTH OXIDE BASED AMMONIA SENSOR

BACKGROUND

With rapid development of modern industry, people are enjoying high-quality life while the accurate detection of toxic and hazardous gases is of special important for environmental safety and human health. Ammonia ($NH_3$), even lower than 50 ppm, can severely irritate human respiratory organs, skin, and eyes (Li, et al., ACS Appl. Mater. Interfaces 2018, 10, 27858). Therefore, the detection and monitoring of $NH_3$ concentration is very important. According to the Occupational Safety and Health Administration (OSHA), the concentration of $NH_3$ in the air should not exceed 25 ppm (17 mg/cm$^3$). Meanwhile, exhaled breath contains more than 1000 volatile organic compounds (VOCs) that are the products of metabolism. Based on clinical findings, a small amount of breath $NH_3$ is biomarker for diagnosis in physiological and pathogenic processes. The concentration of breath $NH_3$ for the end-stage renal disease patients (mean 4.88 ppm; range 0.82-14.7 ppm) is higher than that for healthy human (mean 0.96 ppm; range 0.425-1.8 ppm) (Davies et al., Kidney Int. 1997, 52, 223). Thus, the research of manufacturing high-performance $NH_3$ sensors has attracted extensive attention in environment monitoring and medical diagnosis.

Nowadays, the realization of making $NH_3$ sensors can be conducted by Pt catalyzed silica coating over $WO_3$ thick films (Srivastava, Sens. Actuators, B 2008, 133, 46), flower-shaped $SnS_2$ nanostructures (Xiong, J. Hazard. Mater. 2018, 341, 159), wormlike polypyrrole/graphene heterostructures (Gao, et al., ACS Appl. Mater. Interfaces 2020, 12, 38674), and so on. However, the reported results still suffer from low response speed, limit of detection, and high operating temperature. The preparation of highly sensitive materials for fast detecting low concentration $NH_3$ is one long-term tough assignment for the scientific community.

Bismuth oxide ($Bi_2O_3$) is an important metal oxide semiconductor that widely used in photocatalysis because of its proper band gap ($E_g$=2.58 eV), non-toxicity and low cost. Zhang et al. prepared rod-like $\alpha$-$Bi_2O_3$ and tetrahedral $\gamma$-$Bi_2O_3$ particles with high photocatalytic activity at different temperatures by a facile precipitation method (Zhang, et al., J. Alloys Compound. 2016, 689, 787). Lu et al. prepared $Bi_2O_3$/$Bi_2SiO_5$ p-n heterojunction photocatalyst with large specific surface area and contact angle by one-step calcination of fully mixed $Bi(NO_3)_3$ and nano $SiO_2$ at 600° C. for 4 h (Lu, et al., Appl. Cataly. B 2018, 237, 59). However, the application of $Bi_2O_3$ material in the field of sensors is extremely limited due to low electron mobility and poor performance stability. Kim et al. designed a high sensitivity and high selectivity $NO_2$ sensor based on $Bi_2O_3$ branched $SnO_2$ nanowires by vapor liquid solid method (Kim, et al., Sens. Actuators, B 2018, 274, 356). As compared with the single nanowire sensor, the branched $Bi_2O_3$/$SnO_2$ sensor has higher sensing performance. However, it was felt that it is not the $Bi_2O_3$/$SnO_2$ interface but the compound $Bi_2Sn_2O_7$ phase that is taking part in improved gas-sensing performance. Besides, the large-scale synthesis is limited because of their complex process and high-power consumption. These shortcomings have been perfectly solved in the invention.

The invention adopts a simple one-step hydrothermal method to prepare hierarchical bismuth oxide microspheres and a simple spray technology to prepare bismuth oxide endow renewable seaweed fabrics, and fabricates an ultrasensitive $NH_3$ sensor. The sensor not only exhibits excellent sensitivity, selectivity and stability towards $NH_3$ at room temperature but also possesses excellent flexibility and flame retardancy, providing possibility for the realization of flexible and wearable sensor. The expiratory response of patients with *Helicobacter pylori* infection fully proves that it can be used to detect $NH_3$ in human respiration, which means that it contributes to the development of predictive and personalized medicine. Except for that, the green sources, low cost, low-power consume also fully proves that the sensor based on $Bi_2O_3$ endowed seaweed fabrics ia very worthy to be popularized to production, so as to promote the productivity level.

DETAILED DESCRIPTION

The invention adopts a simple one-step hydrothermal method to prepare the hierarchical bismuth oxide microspheres and a simple spray technology to prepare bismuth oxide endow renewable seaweed fabrics. These three-dimensional (3D) hierarchical microspheres with diameters of 4-6 μm are assembled from two-dimensional (2D) nanosheets with thickness of 10 to 50 nm, ensuring a higher contacting area for the gas adsorption, which could allow the application of devices with excellent performance. The obtained bismuth oxide endow renewable seaweed fabrics ($Bi_2O_3$/SA) displays excellent flexibility, flame retardancy and can withstand deformation (e.g. bending), providing possibility for the realization of flexible and wearable sensor. The flexible gas sensor can work at room temperature, and exhibits high response (1300), ultrashort response/ recovery time (<25 s/10 s), small detection limit (100 ppb), and high selectivity to ammonia. Additionally, the gas sensor displays excellent anti-interference ability, long-term stability and reproducibility. Also, the gas sensor shows excellent response to exhalation in *Helicobacter pylori* infected patients. The above results provide us with the opportunity that a room-temperature operated gas-sensitive oxide semiconductor can be integrated with flexible and renewable seaweed substrate to achieve a smart wearable electronic device for real-time environment monitoring and medical diagnosis.

Figure 1:
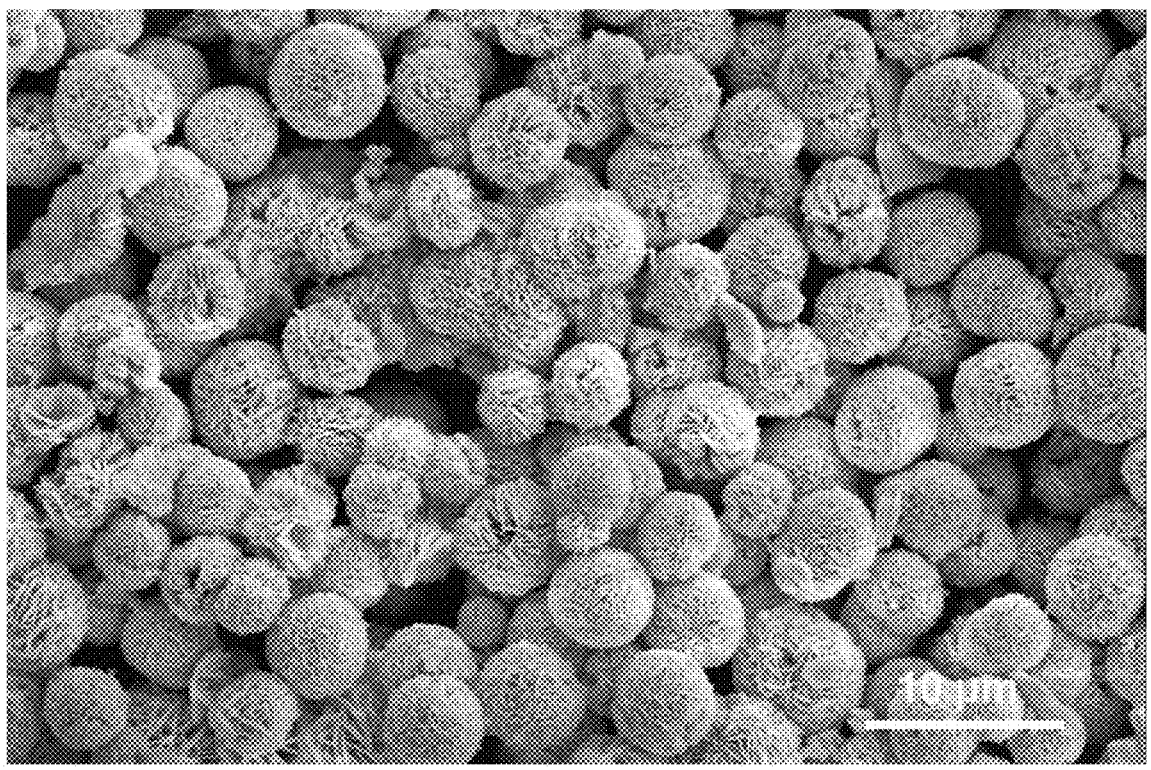
FIG. 1 is a SEM image of the $Bi_2O_3$ material with hierarchical structure according to an embodiment of the invention.
Figure 2:
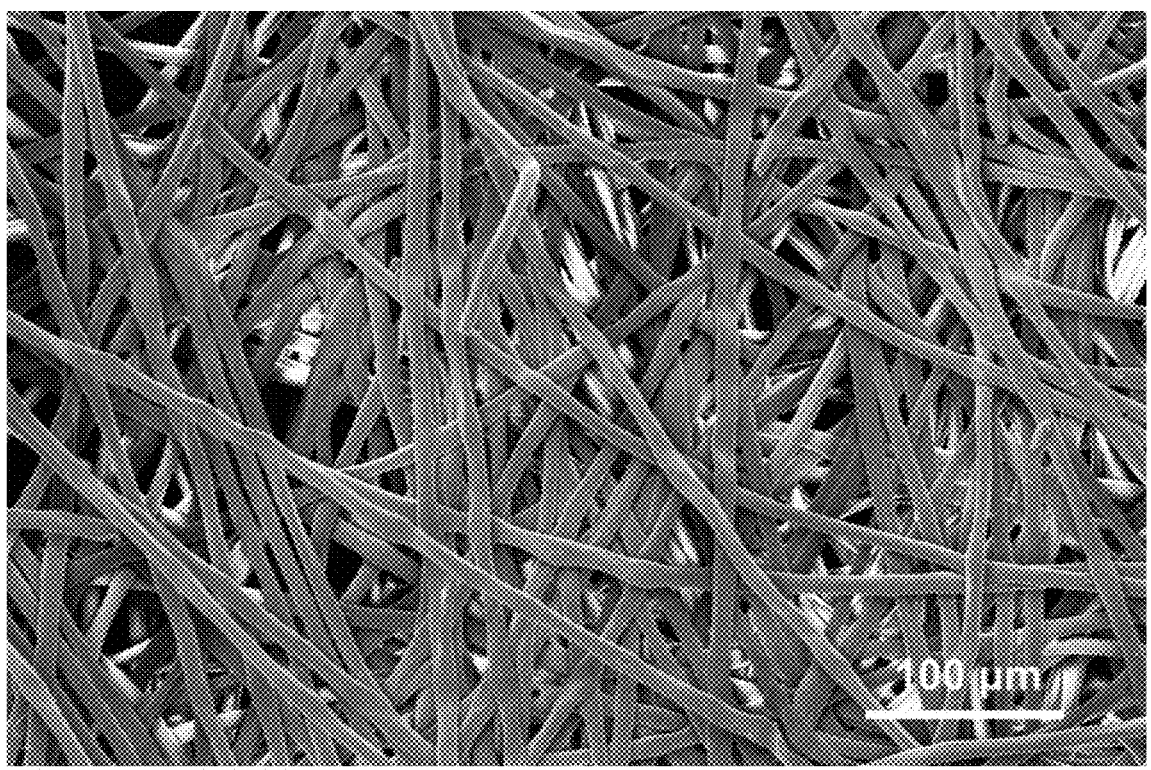
FIG. 2 is a SEM image of the renewable seaweed fabric according to an embodiment of the invention.
Figure 3:
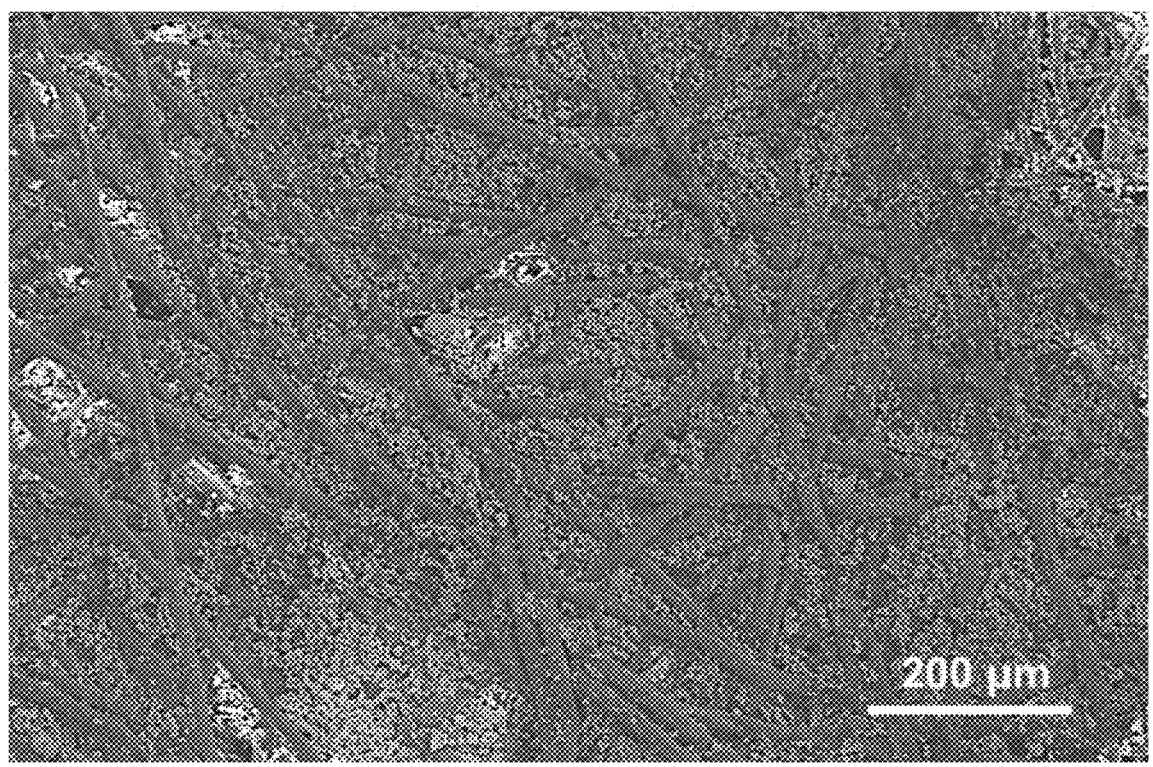
FIG. 3 is a SEM image of the $Bi_2O_3$ endow seaweed fabric according to an embodiment of the invention.
Figure 4:
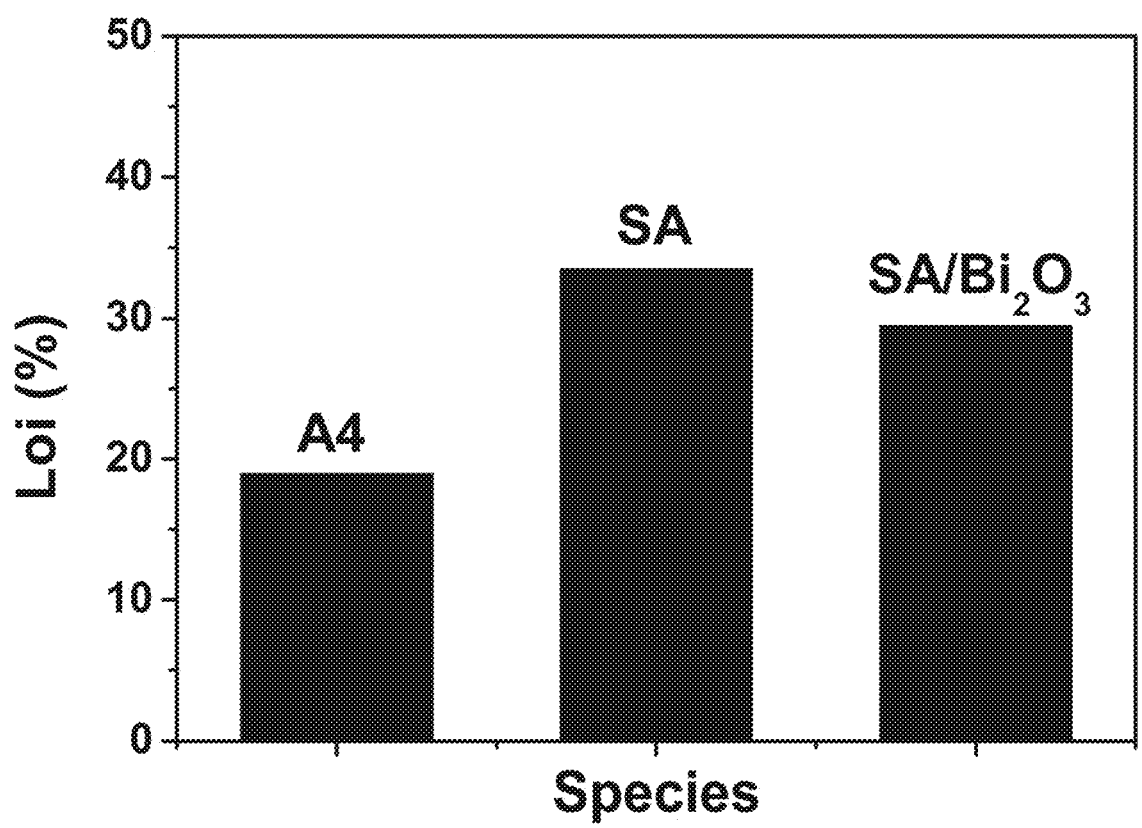
FIG. 4 is the limiting oxygen index (LOI) index refers to the $Bi_2O_3$ endow seaweed fabric according to an embodiment of the invention, as compared with the traditional A4 paper and seaweed fabric (SA).

FIG. 1 shows that the as-synthesized product is a compact aggregate of flower-shape microspheres with diameters of 4-6 μm, and these nanoflowers are actually assembled by many interlaced 2D nanosheets with the thickness in the range of 10-50 nm. Mostly, uniform thickness of nanosheets gather with each other in the spherical way, forming a porosity surface and the hollow interiors. FIG. 2 shows that the renewable seaweed fabric (SA) interweaves with each other, increasing the surface-to-volume ratio. After spraying, numerous of bismuth oxide microspheres are on the surface and interweave of SA fibers (FIG. 3), and the thickness of the $Bi_2O_3$/SA composite layer is about 200 μm. As shown in FIG. 4, the LOI index refers to the minimum concentration of oxygen in a mixture of oxygen and nitrogen which will be used to determine the flammability of the samples. The LOI levels of SA and $Bi_2O_3$/SA are obviously higher than that of traditional A4 paper, revealing the good flammability.

Figure 5:
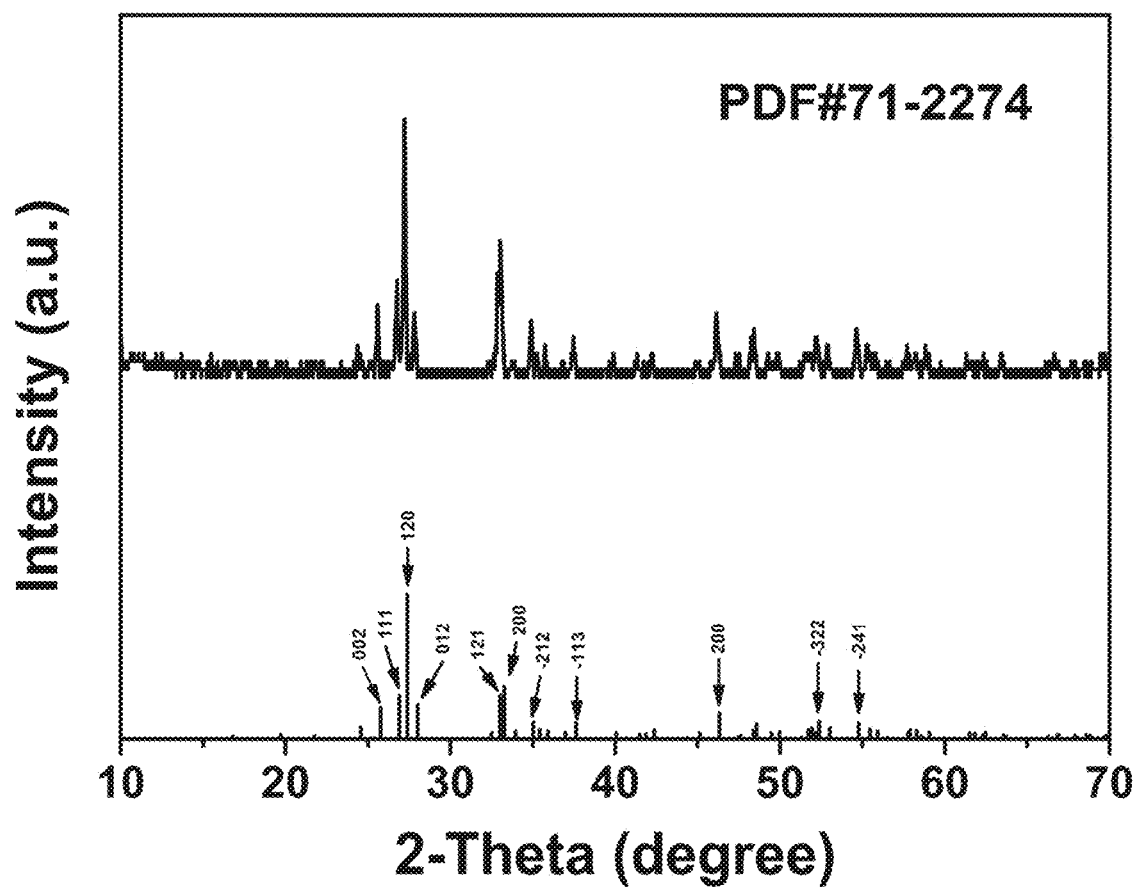
FIG. 5 is the XRD pattern of the annealed $Bi_2O_3$ material according to an embodiment of the invention.

X-ray diffraction (XRD) was used to characterize the crystal structure of the prepared $Bi_2O_3$, as shown in FIG. 5. Each characteristic peak is consistent with the standard card PDF #71-2274, and the main crystal plane spacing d value: 3.4564, 3.3112, 3.2532, 3.1830, 2.7097 and 2.6918 correspond to the crystal planes of (002), (111), (012), (202), (121) and (200) of monocline $Bi_2O_3$ respectively. It can be observed that there is no excess impurity peak in the $Bi_2O_3$ sample.

Figure 6:
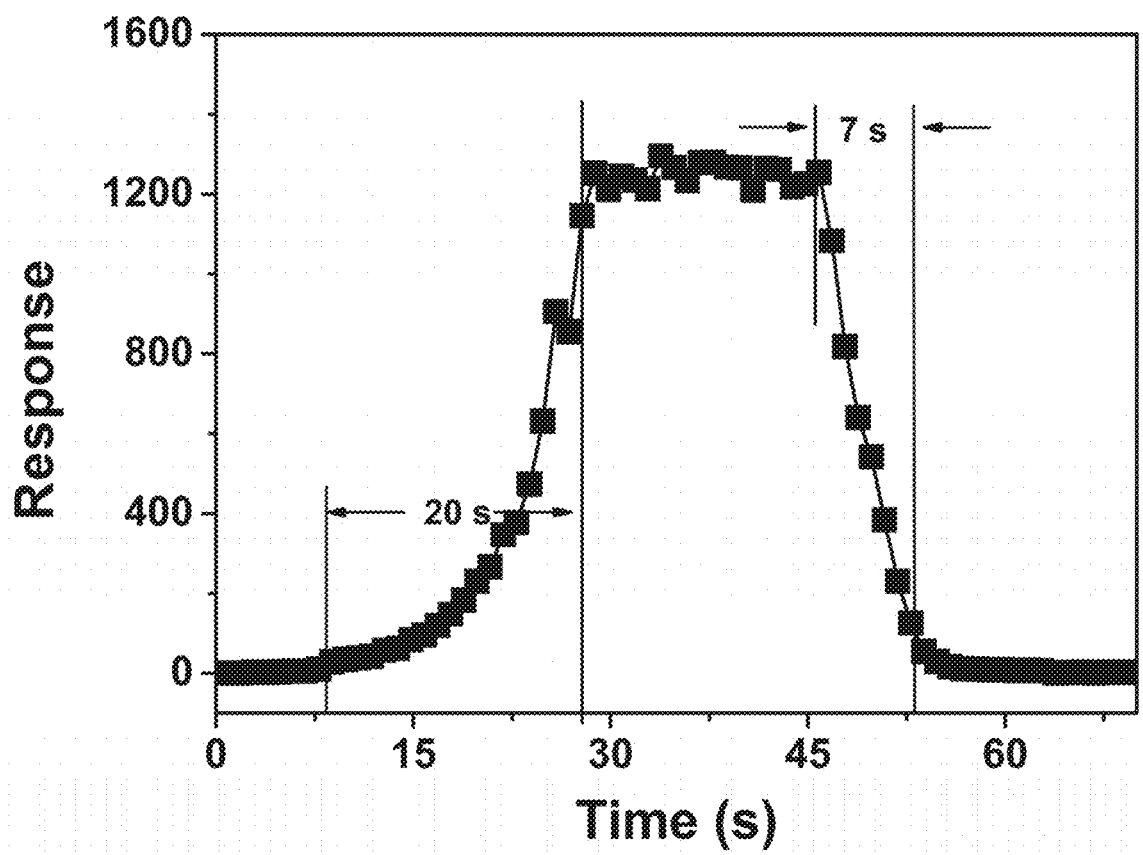
FIG. 6 is a response-recovery curve of a fabricated gas sensor to 20 ppm $NH_3$ according to an embodiment of the invention.

FIG. 6 shows that the response and recovery time of the gas sensor to 20 ppm $NH_3$ at room temperature. When the $Bi_2O_3$ material is exposed to atmosphere, the oxygen molecules are absorbed onto the surface, they capture these free electrons and become $O^{2-}$ irons at room temperature, forming the electron-depletion depletion region and causing high resistance of the $Bi_2O_3$ sensor in air. Upon adsorption of $NH_3$, which is a reductive gas, more electrons transform the substrate, resulting in a decrease in resistance. The whole process takes only 20 s. The large surface area to volume ratio and high porosity of the hierarchical structures can generate abundant channels for $NH_3$ mass transfer and provide abundant active sites, which greatly reduces the gas desorption time (7 s).

Figure 7:
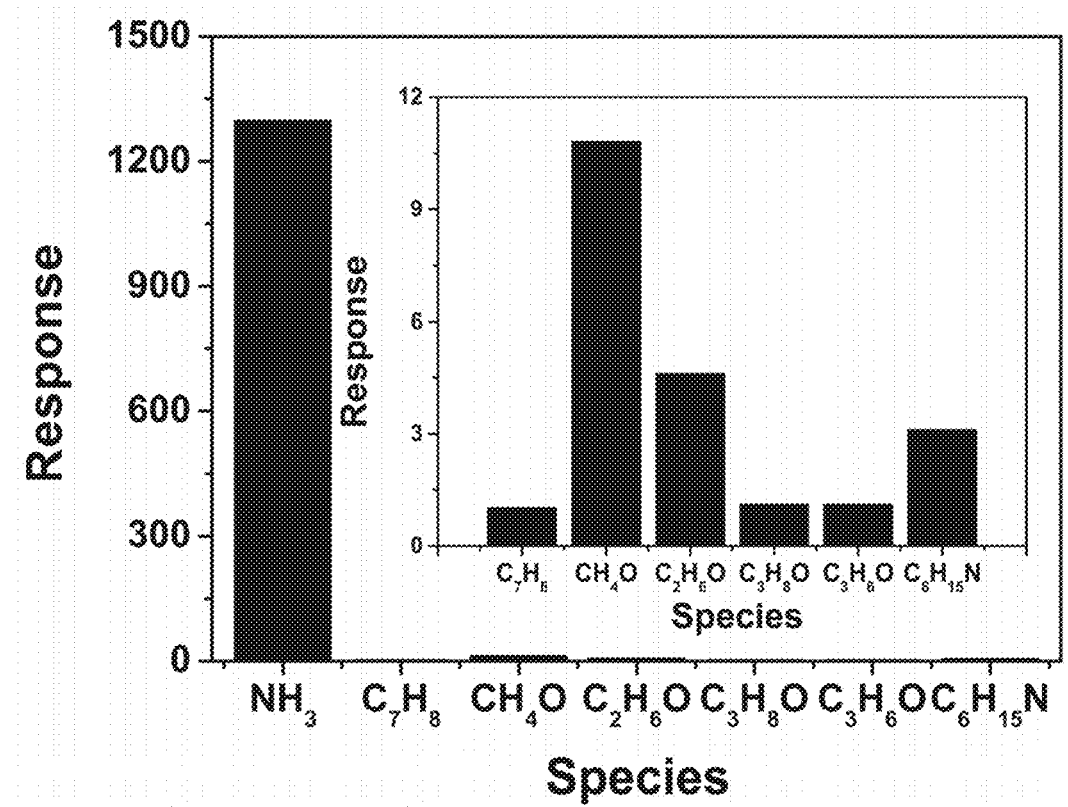
FIG. 7 is the response of a fabricated gas sensor to 20 ppm different gases according to an embodiment of the invention.

The selectivity of the gas sensor is a significant parameter for gas sensors, and we compare the response of the gas sensor toward various gases with a concentration of 20 ppm. As shown in FIG. 7, the sensor exhibits the highest detection response to 20 ppm $NH_3$ (about 1300), and negligible response when exposed to methanol, isopropanol, methanol, ethanol, acetone and triethylamine, indicating weak interference for $NH_3$ detection. The prepared $Bi_2O_3$ material show high response and selectivity towards $NH_3$.

Figure 8:
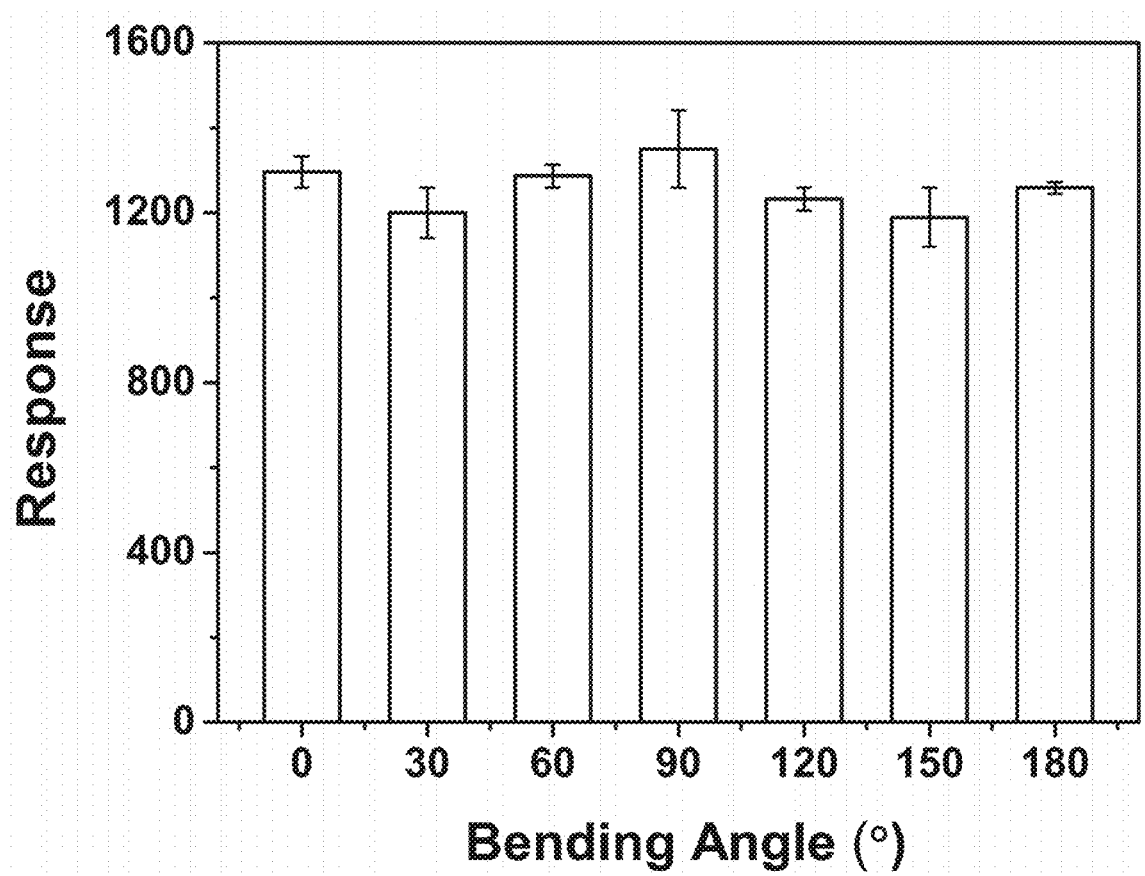
FIG. 8 is the response of a fabricated gas sensor measured under different bending angles according to an embodiment of the invention.

In addition to normal flat state, the $Bi_2O_3$/SA sensor is flexible and can be bend at different angles without losing its gas-sensitive properties (FIG. 8). The response of the gas sensor changes in range of 4%-9%. Meanwhile, inconspicuous changes in response time (1-5 s) and recovery time (3-8 s) can also be nearly ignored, confirming the excellent stability of the sensor.

Figure 9:
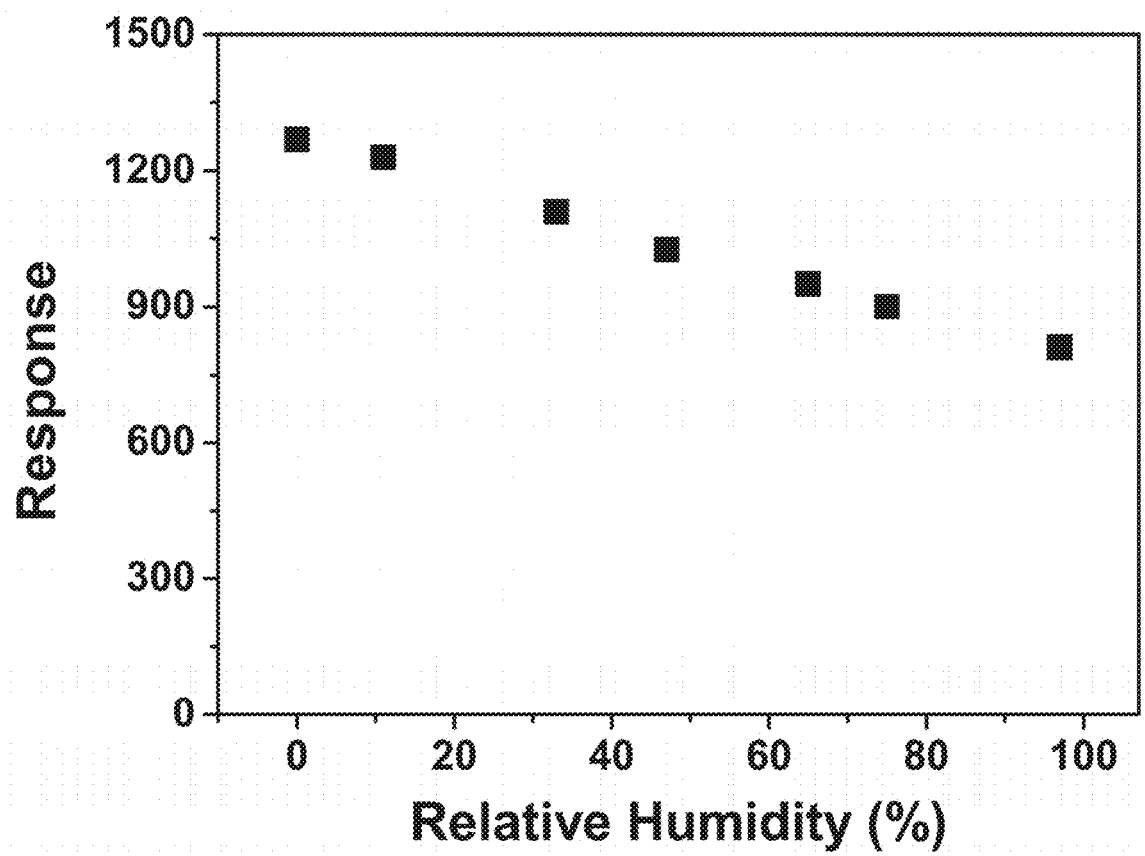
FIG. 9 is the response of a fabricated gas sensor measured under different relative humidity according to an embodiment of the invention.

To explore the effect of relative humidity to the gas sensor, the sensor response were recorded at various humidity conditions (20% RH, 40% RH, 60% RH and 90% RH) at room temperature, as shown in FIG. 9. Apparently, there is a tolerable decrease of the response with the increase of respective RH value of 20-90% RH, because of the interference of water molecules with the surface adsorbed target gas of gas sensor. However, a linear-relationship with R-square of 0.99308 between the response and relative humidity is observed, indicating that the response can be sufficiently predictable in the whole humidity.

Figure 10:
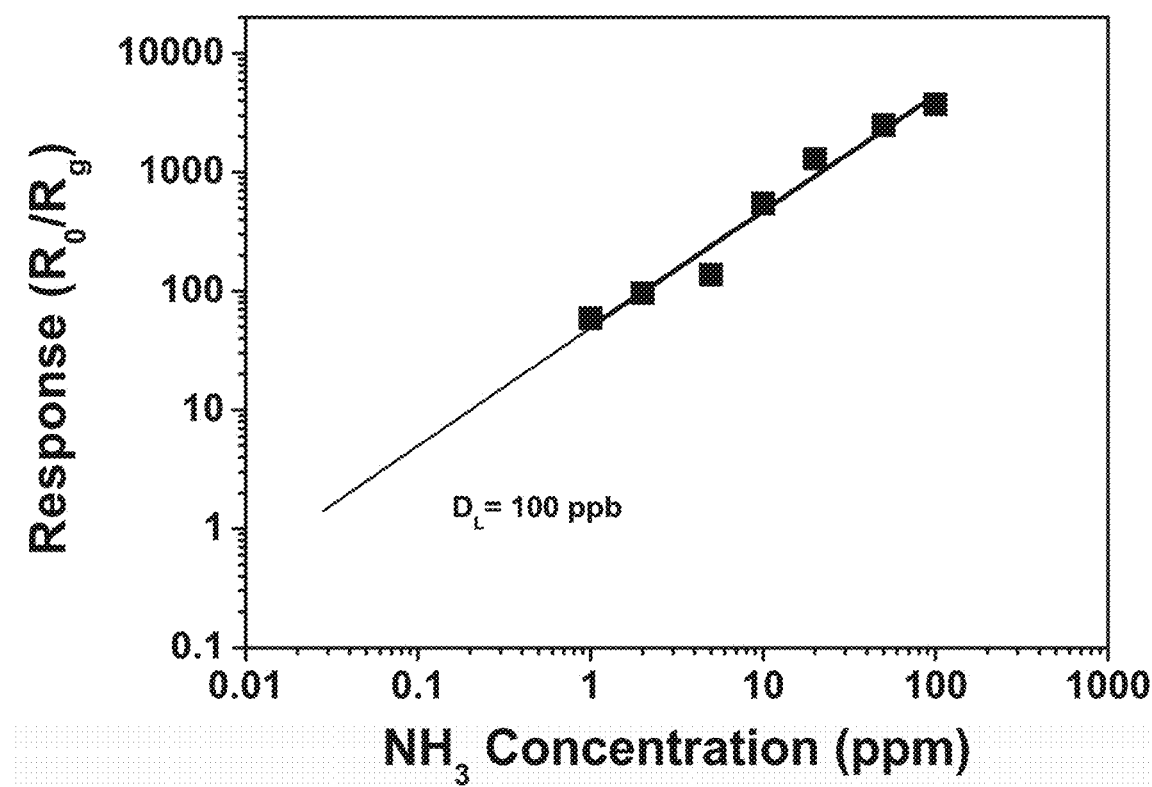
FIG. 10 is the relationships between the sensor response and $NH_3$ concentration according to an embodiment of the invention.

As shown in FIG. 10, the response of the gas sensor has a linear relationship with triethylamine concentration, which was consistent with the law of gradually increasing response. According to the least-squares method of fitting in the linear regime, the theoretical low detection limit ($D_L$) of gas sensor is the value of gas concentration when sensor response is three times greater than the standard deviation of noise signal ($rms_{noise}$). Thus, the theoretical low detection limit of the gas sensor is calculated to be about 100 ppb.

Figure 11:
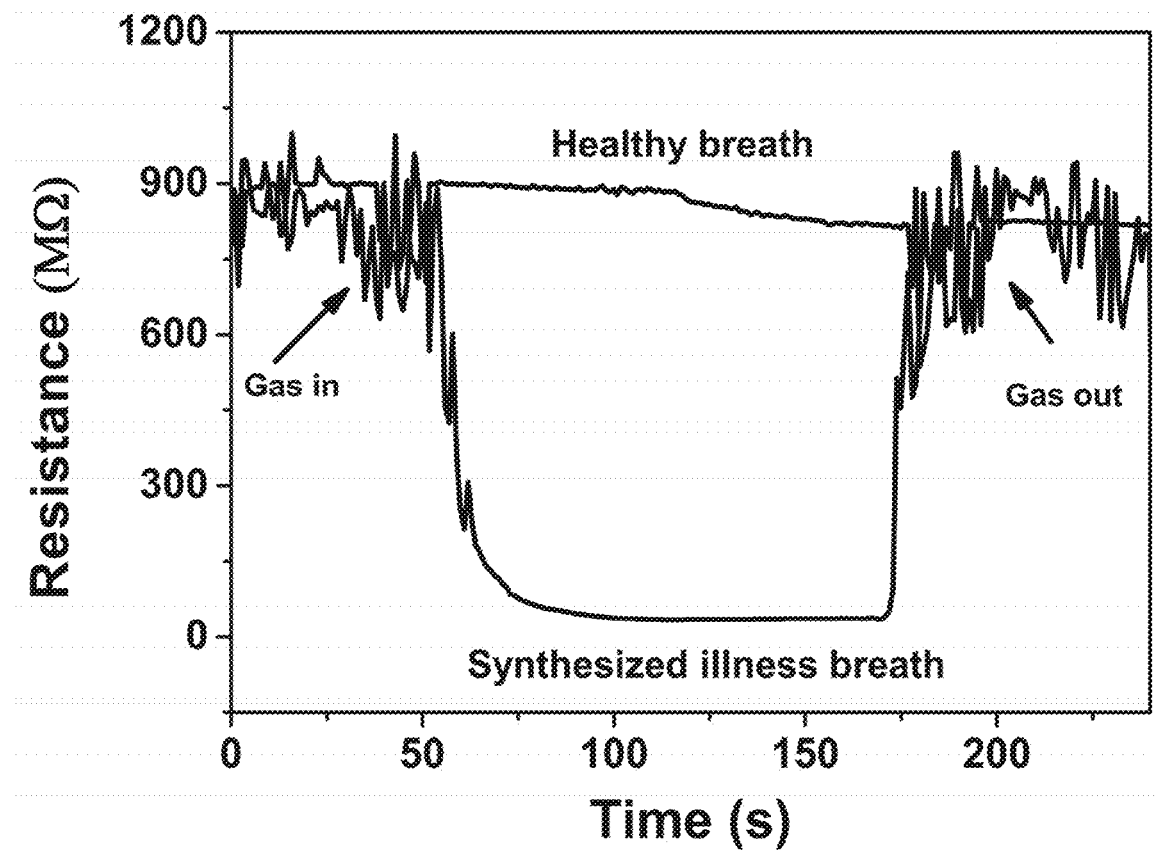
FIG. 11 is the transient curves of a flexible gas sensor upon exposure to a healthy breath and illness breath of a patient with *Helicobacter pylori* infection according to an embodiment of the invention.

To determine the application potential of using the gas sensor for simple medical diagnosis, the gas sensitivity of synthesized illness gas containing trace $NH_3$ respiration is tested. The exhaled breath of healthy people is collected with a 500 mL gas sample bag and injected into the vacuum chamber. For a health breath, the obtained gas has little effect on the sensor resistance (FIG. 11). We then injected 50 ppm of NH3 into a gas sample bag and mixed it with normal exhalation gas to form synthesized illness gas, resting for 1 hour to simulate the exhaled air of *Helicobacter pylori* infected patients. We found that the sensor resistance decreased obviously after synthesized illness gas injection, indicating high potential for feasibility of the flexible gas sensor as new sensing platforms.

Figure 12:
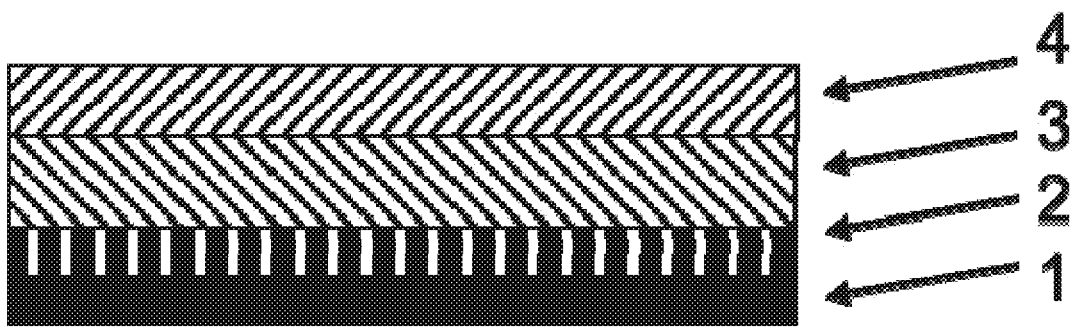
FIG. 12 is the overall structure of a flexible gas sensor according to an embodiment of the invention.

FIG. 12 shows the overall structure of a flexible gas sensor, containing layers of substrate 1, electrode 2, sensitive material 3 and packaging material 4.

Embodiment 1

The pure $Bi_2O_3$ nanosphere is synthesized using a facile one-pot hydrothermal method. In a typical process, 0.97 g of Bi $(NO_3)_3$ is dissolved in the mixture of 34 mL of ethanol and 17 mL of ethylene glycol and kept stirring at room temperature. Then the above mixture is transferred into a 50 ml Teflon-lined stainless-steel autoclave and reacted at 160° C. for 5 h. The white precipitates are collected by centrifugation and washed with absolute alcohol for several cycles, which are air-dried at 60° C. more than 8 h in an oven.

The crystallographic structural and morphology were investigated by X-ray diffraction, (XRD, DX2700) at 40 K and scanning electron microscope (SEM, Quanta 250 FEG) with an energy dispersive spectrometry (EDS) spectrometer. The as-synthesized product is a compact aggregate of flower-shape microspheres with diameters of 4-6 μm, and these nanoflowers are actually assembled by many interlaced 2D nanosheets with the thickness in the range of 10-50 nm. Each characteristic peak is consistent with the standard card PDF #71-2274, and the main crystal plane is in accordance with that of monocline $Bi_2O_3$.

Embodiment 2

A transparent solution was obtained by dissolving 0.5 g of bismuth nitrate pentahydrate ($Bi(NO_3)_3.5H_2O$) in 10 mL of ethylene glycol. Before 60 min of stirring at room temperature, 20 mL of ethanol were added into the above solution.

Then the above mixture is transferred into a 50 ml Teflon-lined stainless-steel autoclave and reacted at 160° C. for 8 h. The white precipitates are collected by centrifugation and air-dried at 60° C. more than 24 h in an oven.

Embodiment 3

The seaweed fibers (SA) with length of 1-2 cm were mixed with deionized water, which was then transferred to a standard fiber dissociator and stirred at 1000 rpm for 20 minutes to ensure that the fibers were evenly dispersed in deionized water. Then, the uniform slurry was quickly transferred to a paper-making apparatus to make SA paper with thickness of 0.4 mm.

A uniform paste was obtained by thoroughly mixing the $Bi_2O_3$ samples with terpineol in an agate mortar, followed by spraying or coating on the SA papers. The above process is repeated several times to form a continuous thin coating on the SA surface. Then, zeolite film was coated on the sensing layer. Finally, the gas sensor element was dried overnight in an oven at 60° C. to improve stability.

The resistance of the sensor in air ($R_0$) or target gas ($R_g$) was tested in a heated vacuum chamber using a source measurement unit (Keithley 2612) with a DC bias voltage of 3 V and a homemade computer control system. The gas response of the sensor in this research was deduced as $S=R_0/R_g$ (for reducing gases). The response time is defined as the time taken from $R_0$ to $R_0-90\%\times(R_0-R_g)$ after injecting the target gas. The recovery time is defined as the time taken from $R_g$ to $R_g+90\%\times(R_0-R_g)$ after removing the gas.

The invention claimed is:

1. A method of detecting ammonia in a user's breath, wherein the ammonia is detected by porous bismuth oxide endowed renewable seaweed fabric.

2. The method of claim 1, wherein the porous bismuth oxide material is prepared by a one-pot hydrothermal method; the method comprising the steps of:
   a) dissolving an amount of bismuth nitrate in a mixture of ethanol and ethylene glycol, and kept stirring at room temperature;
   b) transferring the above mixture into a Teflon®-lined stainless-steel autoclave;
   c) reacting the mixture at 120-160° C. for 2-16 hours;
   d) collecting the precipitates by centrifugation;
   e) washing the product with absolute ethanol and deionized water; and
   f) air-drying the product at 60° C. in an oven for more than 8 h.

3. The method of claim 1, wherein the bismuth oxide material possesses microsphere morphology with diameter of 4-6 μm.

4. The method of claim 3 wherein the microspheres are assembled by multiple interlaced two-dimensional (2D) nanosheets with thickness of 10-50 nm to produce an aggregate.

5. The method of claim 4 wherein the aggregate structure has the appearance of an aggregate of micro-flowers.

6. The method according to claim 1, wherein the renewable seaweed fabrics are fabricated from alginate fibers by wet-spinning and papermaking processes.

7. The method according to claim 1, wherein the thermally treated semiconducting bismuth oxide is combined with renewable seaweed fabrics by a spray technology; preferably wherein the bismuth oxide and renewable seaweed fabric comprise a composite layer having a thickness of about 100-250 μm.

8. A gas sensor for detecting ammonia in the environment, wherein the gas sensor comprises a porous bismuth oxide endowed renewable seaweed fabric.

9. The gas sensor according to claim 8, wherein the gas sensor comprises a flexible gas sensor.

10. The gas sensor according to claim 9, wherein the flexible gas sensor is flame retardant and reproducible at either flat or bent states.

11. The gas sensor according to claim 8, for use in the detection of ammonia in patients having a *helicobacter pylori* infection.

12. The gas sensor according to claim 8, wherein the gas sensor is provided in a wearable medical device.

13. A gas sensor according to claim 12, wherein the wearable medical device is configured to receive, analyze and output physiological health data.

\* \* \* \* \*